(12) United States Patent
Miyazaki et al.

(10) Patent No.: US 9,155,874 B2
(45) Date of Patent: Oct. 13, 2015

(54) MEDICAL ELONGATED BODY

(71) Applicant: TERUMO KABUSHIKI KAISHA, Shibuya-ku (JP)

(72) Inventors: Kaoru Miyazaki, Ashigarakami-gun (JP); Wataru Karino, Fujinomiya (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 21 days.

(21) Appl. No.: 13/852,466

(22) Filed: Mar. 28, 2013

(65) Prior Publication Data

US 2013/0261538 A1 Oct. 3, 2013

(30) Foreign Application Priority Data

Mar. 28, 2012 (JP) .................. 2012-074432

(51) Int. Cl.
*A61M 37/00* (2006.01)
*A61B 17/00* (2006.01)
*A61B 17/12* (2006.01)

(52) U.S. Cl.
CPC .......... *A61M 37/00* (2013.01); *A61B 17/00491* (2013.01); *A61B 17/12022* (2013.01); *A61B 17/12109* (2013.01); *A61B 17/12113* (2013.01); *A61B 17/12186* (2013.01); *A61B 2017/00495* (2013.01)

(58) Field of Classification Search
CPC ............ A61M 37/00; A61B 17/00491; A61B 17/12022; A61B 17/12113; A61B 17/12186; A61B 17/12109; A61B 2017/00495
USPC .......................................... 604/23–26, 82–92
See application file for complete search history.

(56) References Cited

U.S. PATENT DOCUMENTS

| 5,395,318 | A | * | 3/1995 | Kaprelian | ...................... 604/520 |
| 5,887,755 | A | * | 3/1999 | Hood, III | ...................... 222/135 |
| 6,047,861 | A | * | 4/2000 | Vidal et al. | ..................... 222/137 |
| 6,537,246 | B1 | * | 3/2003 | Unger et al. | ..................... 604/82 |
| 6,605,066 | B1 | * | 8/2003 | Gravagna et al. | ............. 604/191 |
| 6,610,043 | B1 | | 8/2003 | Ingenito | |
| 6,620,125 | B1 | * | 9/2003 | Redl | ................................ 604/83 |
| 8,198,365 | B2 | | 6/2012 | Ingenito et al. | |
| 8,469,924 | B2 | * | 6/2013 | Nguyen et al. | ................... 604/89 |

(Continued)

FOREIGN PATENT DOCUMENTS

| JP | 2003-507130 A | 2/2003 |
| JP | 2010-526914 A | 8/2010 |

(Continued)

*Primary Examiner* — Theodore Stigell
(74) *Attorney, Agent, or Firm* — Buchanan Ingersoll & Rooney PC

(57) ABSTRACT

Disclosed herein is a medical elongated body including: a first channel through which a first liquid flows; a second channel through which a second liquid different from the first liquid in liquid composition flows; a mixing section at which the first channel and the second channel join and in which the first liquid and the second liquid are mixed; a gas channel through which a gas flows; a gas mixing-in section adapted to mix the gas into at least one of the first liquid flowing through the first channel and the second liquid flowing through the second channel or into a liquid mixture formed by mixing in the mixing section; a foaming member adapted to convert the liquid containing the gas mixed therein to a foamed material to be discharged; and a discharge port through which the foamed material to be discharged is discharged.

5 Claims, 11 Drawing Sheets

(56) References Cited

U.S. PATENT DOCUMENTS

| | | | |
|---|---|---|---|
| 8,753,670 B2* | 6/2014 | Delmotte | 424/443 |
| 2003/0023202 A1* | 1/2003 | Nielson | 604/80 |
| 2007/0016128 A1* | 1/2007 | Keller | 604/89 |
| 2009/0234326 A1* | 9/2009 | Hayakawa | 604/518 |
| 2014/0228745 A1* | 8/2014 | Sharma et al. | 604/82 |

FOREIGN PATENT DOCUMENTS

| | | |
|---|---|---|
| WO | WO 01/13908 A2 | 3/2001 |
| WO | WO 2008/141059 A1 | 11/2008 |

* cited by examiner

MEDICAL ELONGATED BODY

CROSS-REFERENCE TO RELATED APPLICATION

This application is based on Japanese Patent Application No. 2012-074432 filed on Mar. 28, 2012, the contents of which are incorporated herein by reference.

BACKGROUND

1. Technical Field

The present invention relates to a medical elongated body (an elongated body for medical use) which is used for discharging a foamed material to be discharged.

2. Description of Related Arts

Hitherto, there has been known a technique of mixing two kinds of in vivo injections and a gas with one another to produce a foamed material to be discharged, and administering the foamed material to be discharged into a living body (see, for example, JP-T-2003-507130 (hereinafter referred to as Patent Document 1)). The in vivo injections used in the technique described in Patent Document 1 have a problem in that, immediately upon mixing of the injections, a polymerization reaction takes place and gelation proceeds, so that the foamed material to be discharged cannot be distributed sufficiently to a peripheral part of the living body organ which is the target of administration.

On the other hand, JP-T-2010-526914 (hereinafter referred to as Patent Document 2) discloses a pulmonary emphysema treating method in which a foamed therapeutic agent or sealing agent is produced from in vivo injections requiring a certain period of time until the occurrence of a polymerization reaction and is administered. This therapeutic method makes it possible to enhance the delivery properties of the foamed material to be discharged in the living body, as compared with the method disclosed in Patent Document 1. However, the operations of producing the foamed material to be discharged and administering the foamed material are troublesome, for the following reason. In the method disclosed in Patent Document 2, the foamed material to be discharged is produced by use of a plurality of in vivo injection syringes for respectively holding in vivo injections which differ in liquid composition. Utilizing the plurality of syringes, mixing of the in vivo injections and mixing of the gas are repeated, whereby the foamed material to be discharged is produced from the therapeutic agent or sealing agent and the like. Then, a predetermined quantity of the thus produced foamed material to be discharged is administered by an exclusive-use catheter device which is provided separately from the syringes.

SUMMARY

According to the method of Patent Document 2, therefore, an operation of producing the foamed material to be discharged by use of various syringes and a further operation of connecting the syringe to the exclusive-use catheter device for administering the foamed material are needed. Thus, much labor is required for the production and administration of the foamed material to be discharged.

It is an object of the present invention to provide a medical elongated body by which laborious operations of producing and administering a foamed material to be discharged can be omitted, and a desired technique or procedure can be carried out easily and speedily.

According to the present invention, there is provided a medical elongated body by which a foamed material to be discharged is discharged, the medical elongated body including: a first channel through which a first liquid flows; a second channel through which a second liquid different from the first liquid in liquid composition flows; a mixing section at which the first channel and the second channel join and in which the first liquid and the second liquid are mixed; a gas channel through which a gas flows; a gas mixing-in section adapted to mix the gas into at least one of the first liquid flowing through the first channel and the second liquid flowing through the second channel or into a liquid mixture formed by mixing in the mixing section; a foaming member adapted to convert the liquid containing the gas mixed therein to a foamed material to be discharged; and a discharge port through which the foamed material to be discharged is discharged.

When the first liquid and the second liquid differing in liquid composition are made to flow into the medical elongated body, it is ensured that a series of operations involving mixing of the liquids, mixing of the gas into the liquid(s), foaming of the liquid(s) containing the gas mixed therein, and discharge of the foamed material to be discharged, can be carried out smoothly. Therefore, the laborious operations for the production and discharge of the foamed material to be discharged can be omitted. Consequently, various procedures for administering a foamed material to be discharged into a living body can be performed easily and speedily.

In the medical elongated body as above, preferably, the mixing section has a plurality of communication channels each establishing communication between the first channel and the second channel.

This configuration ensures that the first liquid and the second liquid can be mixed with each other through the plurality of communication channels, during the flow of the first liquid through the first channel and during the flow of the second liquid through the second channel. Therefore, the liquids can be mixed with each other favorably, without hindering smooth flow of each of the liquids in the medical elongated body.

In the medical elongated body as above, preferably, the plurality of communication channels include a first communication channel of which channel sectional area gradually decreases from the first channel toward the second channel, and a second communication channel of which channel sectional area gradually decreases from the second channel toward the first channel.

This configuration permits the first liquid to easily flow from the first channel toward the second channel, and permits the second liquid to easily flow from the second channel toward the first channel. Therefore, the first liquid and the second liquid can be uniformly mixed together in the mixing section. Consequently, the concentrations of the ingredients of the foamed material to be discharged as a whole can be prevented from being dispersed, at the time of discharge of the foamed material.

In the medical elongated body as above, preferably, the mixing section is provided with at least either of a plurality of granular members and a plurality of line-shaped members.

This configuration permits the mixing to be achieved while the first liquid and the second liquid are passing through the channels defined by the granular members or line-shaped members provided in the mixing section. Consequently, the mixing can be carried out more uniformly than in the case where the mixing is effected by simply causing one of the liquids to mix into the flow of the other of the liquids.

In the medical elongated body as above, preferably, the mixing section has a stirring channel through which the first liquid, the second liquid, and the gas are made to flow under stirring.

This configuration enables the liquids and the gas to be stirred during when they flow. Therefore, the first liquid and the second liquid can be uniformly mixed together in the mixing section.

In the medical elongated body as above, preferably, the gas mixing-in section has a porous member which is provided in the gas channel and which is exposed to at least one of the first channel and the second channel.

This configuration ensures that the gas in the form of bubbles released from the porous member can be dispersely mixed into each of the liquids. Consequently, foaming of the liquid containing the gas mixed therein can be promoted.

In the medical elongated body as above, preferably, the foaming member is at least disposed at the discharge port.

This configuration ensures that the foaming of the liquid is performed at the time of discharge. Therefore, it is possible to obviate a situation wherein the material to be discharged that is once foamed in the medical elongated body might be liquefied, to be discharged as a liquid. Consequently, assured discharge of a foamed material to be discharged can be realized.

The medical elongated body as above, preferably, further includes an auxiliary mixing member which is disposed on a distal side relative to the mixing section and by which the liquid mixture is mixed.

The arrangement of the auxiliary mixing member makes it possible to mix the first liquid and the second liquid with each other more uniformly.

In the medical elongated body as above, preferably, the gas mixing-in section has a gas delivery port adapted to deliver the gas from a position on a proximal side relative to the mixing section toward the mixing section.

This configuration ensures that the gas is delivered through the gas delivery port arranged on the proximal side relative to the mixing section, whereby the gas can be made to blow through the mixing section. Therefore, the liquid mixture can be prevented from stagnating or remaining in the mixing section. Consequently, the mixing section can be prevented from being clogged up.

DETAILED DESCRIPTION OF THE INVENTION

Figure 1:
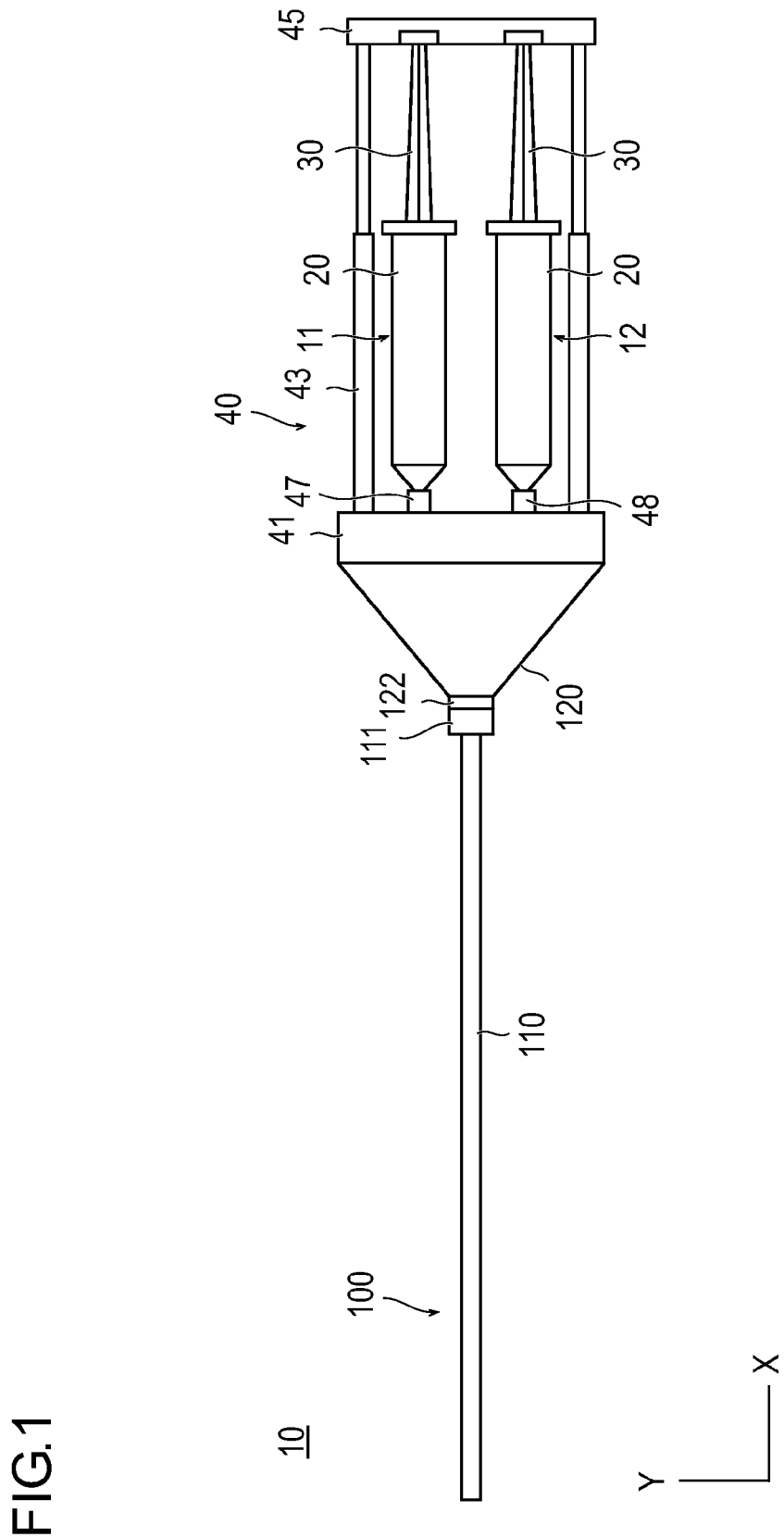
FIG. 1 is a plan view showing the general configuration of an applicator provided with a medical elongated body according to a first embodiment of the present invention.

Now, some embodiments of the present invention will be described below, referring to the drawings. Incidentally, the dimensional proportions in the drawings are exaggerated for convenience of illustration, and may therefore be different from the actual proportions.

First Embodiment

Figure 2:
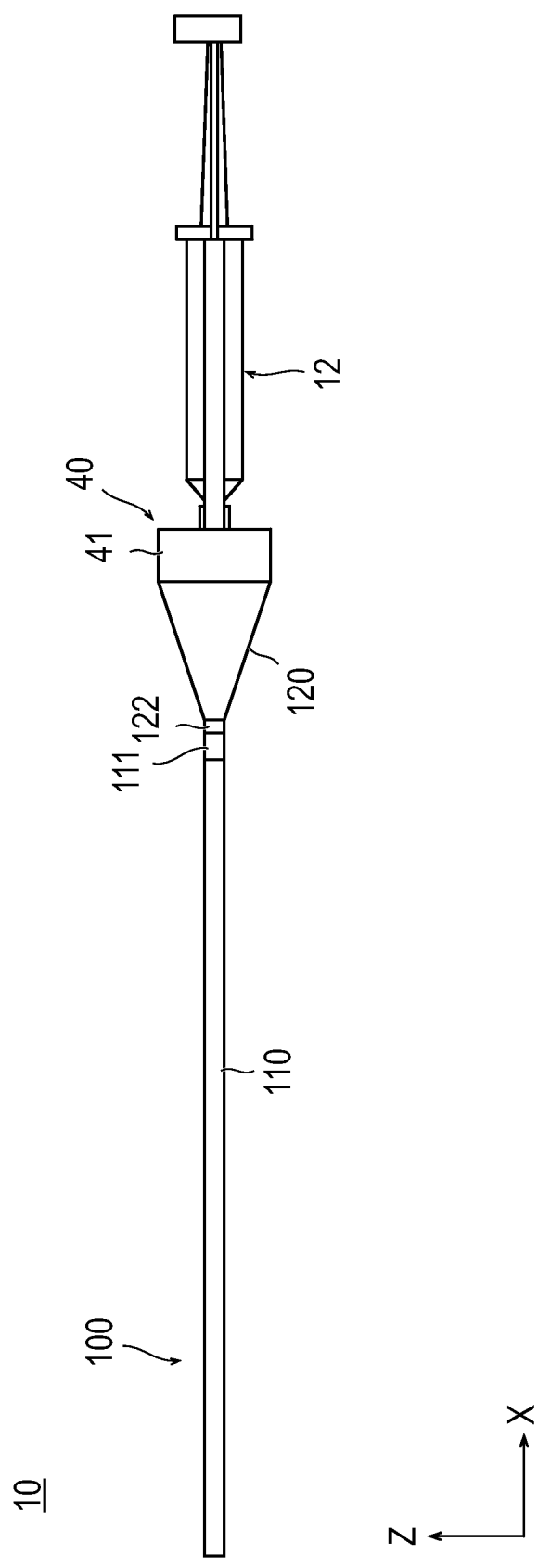
FIG. 2 is a side view showing the general configuration of the applicator.
Figure 3:
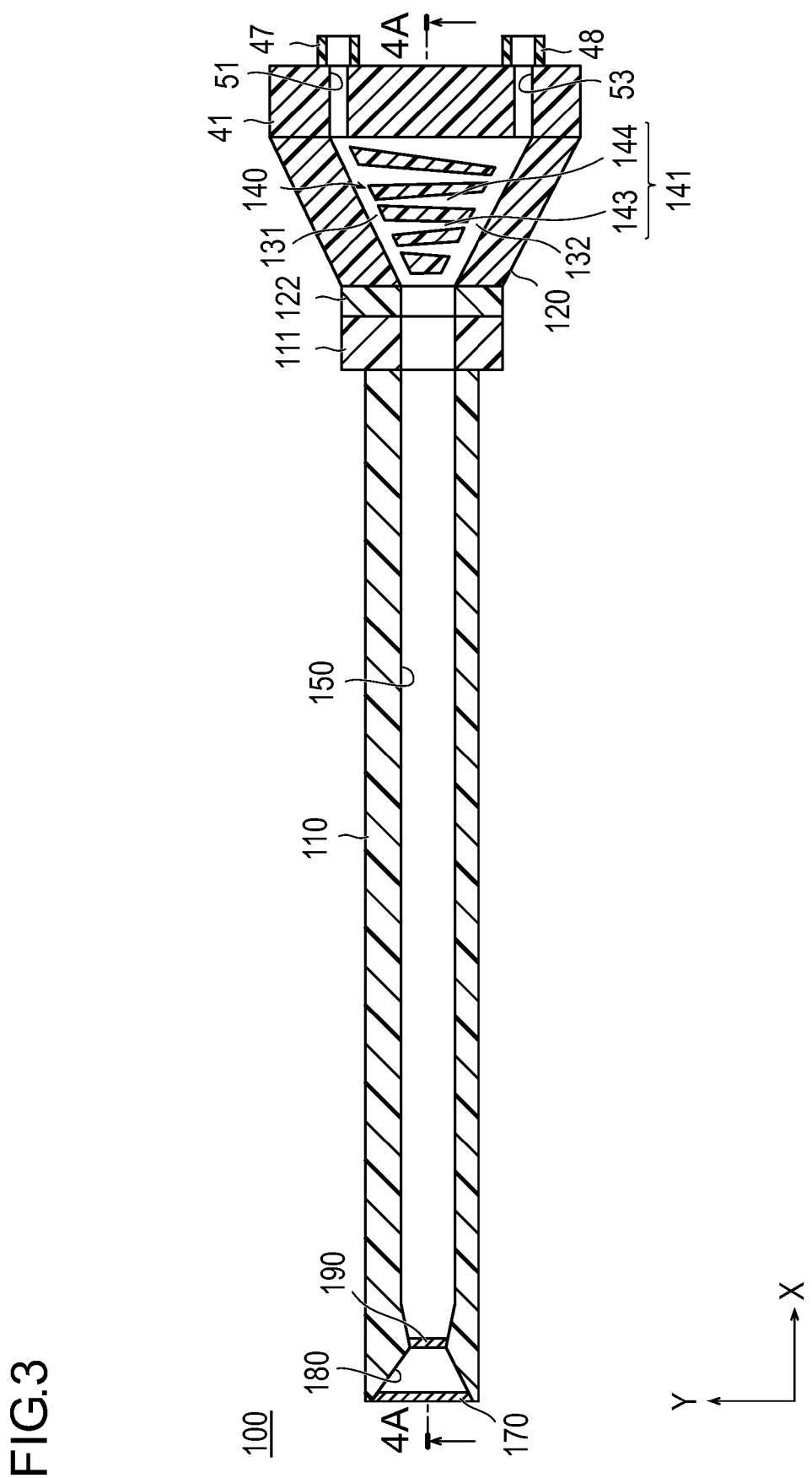
FIG. 3 is a view for illustrating the medical elongated body according to the first embodiment, and is an enlarged sectional view of the medical elongated body along the left-right direction of FIG. 1.
Figure 4:
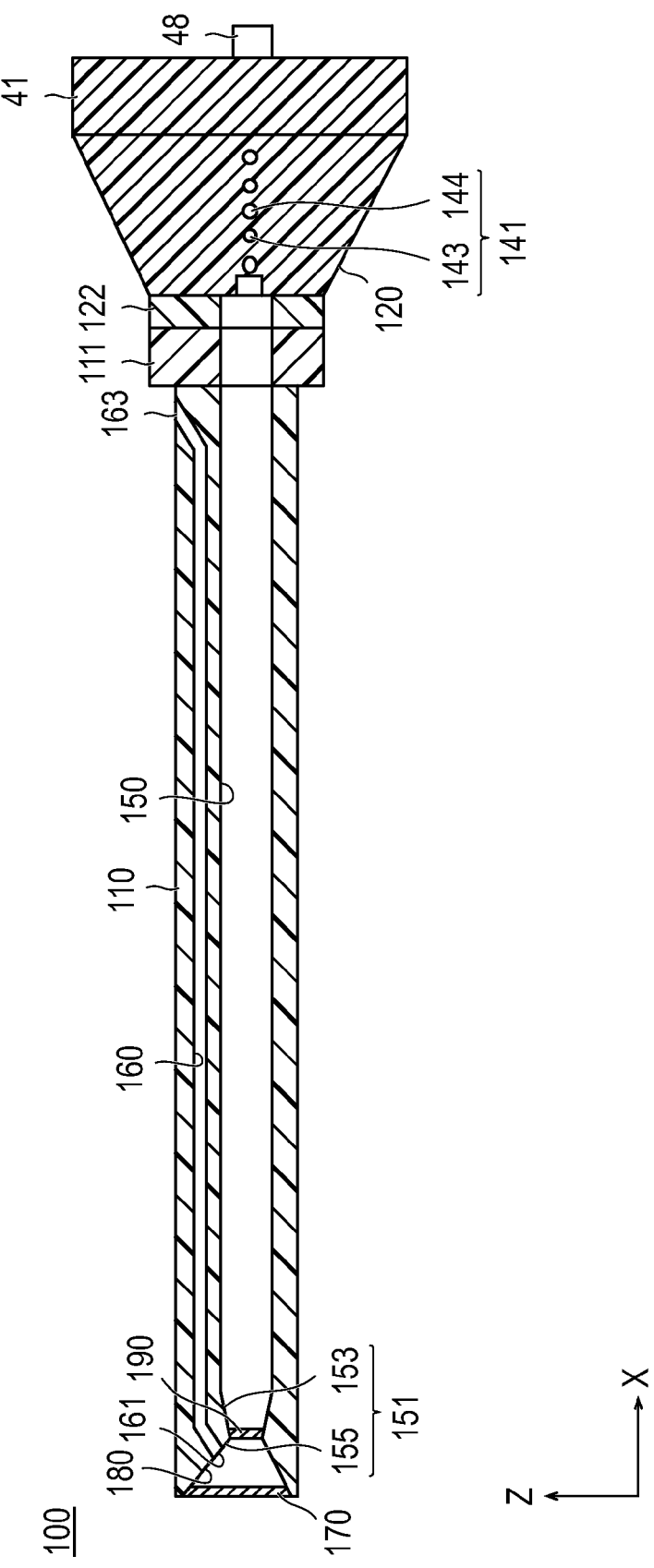
FIG. 4 is a view for illustrating the medical elongated body according to the first embodiment, and is an enlarged view of the medical elongated body taken along line 4A-4A of FIG. 3.
Figure 5:
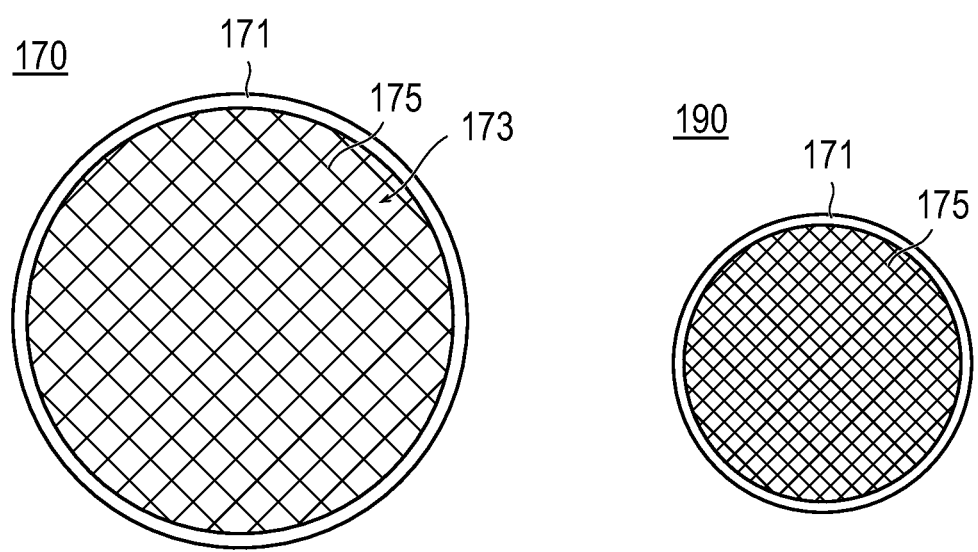
FIG. 5 shows a foaming member and an auxiliary mixing member to be used in the medical elongated body.

FIGS. 1 and 2 illustrate the general configuration of an applicator provided with a medical elongated body according to a first embodiment of the present invention, FIGS. 3 and 4 are partly sectional views for illustrating the medical elongated body, and FIG. 5 illustrates a foaming member and an auxiliary mixing member to be used in the medical elongated body. In the drawings, plane X-Y is a plane in the case of viewing the medical elongated body from the upper side, while plane X-Z is a plan in the case of viewing the medical elongated body from a lateral side.

A medical elongated body 100 according to the present invention is an elongated member by which a liquid made to flow into the medical elongated body 100 from the exterior is foamed, to be discharged as a foamed material to be discharged. As shown in FIGS. 1 and 2, the medical elongated body 100 can be used, for example, together with syringes 11 and 12 for holding various liquids or with an operating member 40 provided so that the medical elongated body 100 and the syringes 11, 12 can be mounted thereto. In addition, these members can constitute an applicator (medical device) 10 for applying the foamed material to be discharged to a predetermined part of a living body. In the following, the medical elongated body 100 according to the present embodiment will be described together with the applicator 10. In the description herein, the left side in FIGS. 1 to 4, or the forward side with respect to the extending direction of the medical elongated body 100, will be referred to as "distal (side)," and the right side in FIGS. 1 to 4, or the backward side with respect to the extending direction of the medical elongated body 100, as "proximal (side)."

As shown in FIGS. 1 and 2, the applicator 10, in general, includes the medical elongated body 100, the first syringe 11 and the second syringe 12 which are so provided as to be connectable to and disconnectable from the medical elongated body 100, and the operating member 40 to be used for causing the liquids contained in the syringes 11 and 12 to flow into the medical elongated body 100.

The purpose of use of the applicator 10 is not specifically restricted. Examples of the purpose of use include injection of a medicinal liquid or medical material into a living body, sealing of living body tissues or lumen, hemostasis, embolization of a circulatory organ (such as blood vessel and aneurysm), embolization or sealing of respiratory system (such as bronchial tube and alveoli), sealing and prevention of adhesion on pleura, filling of an articular cavity with a medical material, and other various medical activities by combination of them.

Each of the syringes 11 and 12 includes an outer tube 20 for holding a liquid therein, and a pusher 30 for pushing out the liquid held in the outer tube 20 to an injection port (not shown) located at the distal end (tip), and is any one of those in common use in medical fields. The injection ports of the syringes 11, 12 can be connected respectively to connecting members 47, 48 provided at a base portion 41 of the operating member 40.

The first syringe 11 holds therein a first liquid to be made to flow into a first channel 131 in the medical elongated body 100, whereas the second syringe 12 holds therein a second liquid to be made to flow into a second channel 132 in the medical elongated body 100 (see FIG. 3).

The first liquid and the second liquid to be used in this embodiment are appropriately selected according to such factors as the purpose of use of the applicator 10. For example, where the applicator 10 is used for administration of an adhesive for living body tissues, one of the first liquid and the second liquid may be a liquid (solution or the like) containing thrombin, and the other may be a liquid (solution or the like) containing fibrinogen.

Besides, for example, where the applicator 10 is used for administration of an adhesion-preventing agent, one of the first liquid and the second liquid may be a liquid (solution or the like) which contains succinimidyl-modified carboxymethyldextrin, and the other may be a liquid (solution or the like) which contains disodium hydrogenphosphate.

Incidentally, in this embodiment and embodiments which will be described later, a configuration in which a foamed material to be discharged is formed from two kinds of liquids differing in liquid phase is shown as an example. In utilizing the medical elongated body, however, it suffices that two or more liquids differing in liquid phase at least are used; for instance, a plurality of liquids may further be used according to the intended use.

The material forming the outer tube 20 possessed by each of the syringes 11, 12 is not specifically restricted. Examples of the material include polyvinyl chloride, polyethylene, polypropylene, cyclic polyolefins, and polystyrene. The outer tube may be formed from a transparent material so as to enable external visual checking of the quantity of liquid therein, or the outer tube may be provided thereon with graduations for indicating the quantity of liquid therein. In addition, the internal volumes of the outer tubes of the syringes 11 and 12 may be set different from each other according to the mixing ratio in mixing the first liquid and the second liquid.

As shown in FIGS. 1 to 4, the operating member 40 includes the base portion 41 mounted to a connecting section 120 of the medical elongated body 100, pressing members 43 fixed to the base portion 41, and a rear plate 45 so provided that proximal ends of the pushers 30 of the syringes 11 and 12 can be held thereby.

The material forming the operating member 40 is not particularly restricted. Examples of the material include various metallic materials and various plastic materials, which may be used either singly or in combination.

The pressing members 43 may each be made up of, for example, a rod or a piston or the like so provided that it can be moved forward and backward. In addition, as each of the connecting members 47, 48, for example a fitting-type connector can be used which is formed to be hollow and to which the injection port of each of the syringes 11, 12 can be connected in a liquid-tight and gas-tight manner by insertion.

The connecting member 47 is so provided that the first syringe 11 can be connected thereto, while the connecting member 48 is so provided that the second syringe 12 can be connected thereto. In use of the applicator 10, the syringes 11 and 12 are so set that the proximal ends of the pushers 30 thereof are held at the rear plate 45 of the operating member 40, and that the injection ports located at the distal ends (tips) thereof are connected respectively to the connecting members 47, 48 provided at the base portion 41 of the operating member 40.

The connecting members 47, 48 possessed by the operating member 40 are so disposed that inside spaces of the connecting members 47, 48 communicate respectively with channels 51, 53 defined inside the base portion 41 of the operating member 40 (see FIG. 3). In addition, the channel 51 provided in the base portion 41 of the operating member 40 is so arranged as to communicate with the first channel 131 in the medical elongated body 100, whereas the channel 53 provided in the base portion 41 of the operating member 40 is so arranged as to communicate with the second channel 132 in the medical elongated body 100. Therefore, with the syringes 11 and 12 mounted to the operating member 40, it can be ensured that the inside spaces of the outer tubes 20 of the syringes 11, 12, the inside spaces of the connecting members 47, 48 possessed by the operating member 40, the channels 51, 53 in the base portion 41 of the operating member 40, and the first channel 131 and the second channel 132 in the medical elongated body 100 communicate with one another, respectively. Then, the user of the applicator 10 pushes the rear plate 45 of the operating member 40 toward the distal side (tip side) in the condition where the members have been assembled, whereby the pushers 30 of the syringes 11, 12 can be advanced toward the distal side (tip side), and the respective liquids can be made to flow from the syringes 11, 12 into the inside of the medical elongated body 100.

Incidentally, the configuration of the operating member 40 as shown in the drawings is merely one example, and, naturally, the configuration can be modified according to such factors as the purpose of use of the applicator 10.

Referring to FIGS. 3 and 4, the medical elongated body 100 includes an elongated flexible body section 110, a first connecting member 111 mounted to the body section 110, the connecting section 120 provided on the proximal side (base end side) of the body section 110, and a second connecting member 122 which is provided on the connecting section 120 and can be connected to the first connecting member 111.

As each of the first connecting member 111 and the second connecting member 122, for example, a fitting-type connector can be used which is formed to be hollow and which can be connected to each other in a liquid-tight and gas-tight manner. Besides, while the connecting section 120 of the medical elongated body 100 is preliminarily mounted integrally to the base portion 41 of the operating member 40 in the example shown in the drawings, a configuration may be adopted in which the connecting section 120 of the medical elongated body 100 and the base portion 41 of the operating member 40 are separably connected to each other.

The body section 110 and the connecting section 120 of the medical elongated body 100 may each be formed from a hard material, or may each be a flexible section formed from a flexible material, an elastic material or the like. In this embodiment, these sections are flexible ones. Examples of the material forming each of these sections include polyvinyl chloride, polyvinyl acetate, polyethylene-vinyl acetate copolymer, polyethylene, polypropylene, cyclic polyolefin, polybutadiene, polyurethane, polyurethane elastomer, polyimides, polyamides, polyether bock amide copolymers, polyesters, polyester elastomers, silicone resins, polytetrafluoroethylene and the like fluoro-resins, and polyether-ether ketone resins. Besides, the outside diameter of the body section 110 is not particularly limited insofar as it enables exhibition of the function of the body section 110 in a living body. For instance, the outside diameter may be set in the range of 0.5 to 5 mm, preferably 0.7 to 3 mm.

The connecting section 120 of the medical elongated body 100 is provided therein with the first channel 131 through which the first liquid flows, the second channel 132 through which the second liquid flows, and a mixing section 140 at which the first channel 131 and the second channel 132 join and in which the first liquid and the second liquid are mixed. In addition, the body section 110 is provided therein with a flow lumen 150 through which a liquid mixture formed upon mixing of the first liquid and the second liquid flows, a gas channel 160 through which a gas flows, a gas mixing-in section 161 in which a predetermined gas is mixed into the liquid mixture flowing through the flow lumen 150, a foaming member 170 adapted to convert the liquid with the gas mixed therein to a foamed material to be discharged, and a discharge port 180 through which the foamed material to be discharged is discharged.

The first liquid supplied from the first syringe 11 flows into the first channel 131, whereas the second liquid supplied from the second syringe 12 flows into the second channel 132. The liquids thus flowing in are mixed with each other in the mixing section 140, before being foamed by the foaming member 170. The first liquid and the second liquid differing in liquid composition are sufficiently mixed with each other in the mixing section 140, whereby the concentrations of ingredients of the material to be discharged as a whole can be prevented from scattering when the material is discharged as the foamed material to be discharged. Incidentally, while the first channel 131, the second channel 132 and the mixing section 140 are provided in the connecting section 120 of the medical elongated body 100 in this embodiment, they may for example be provided in the body section 110 of the medical elongated body 100, as shown in an embodiment which will be described later.

As shown in FIGS. 3 and 4, the mixing section 140 may be provided therein with a plurality of communication channels 141 through which the first channel 131 and the second channel 132 communicate with each other. With such communication channels 141 provided, it is possible to mix the first liquid and the second liquid with each other through the plurality of communication channels 141 during the flow of the first liquid through the first channel 131 and during the flow of the second liquid through the second channel 132.

In addition, in order to realize more efficient mixing of the liquids by the communication channels 141, there may be provided, for example, first communication channels 143 each having a channel sectional area gradually decreasing from the first channel 131 toward the second channel 132, and second communication channels 144 each having a channel sectional area gradually decreasing from the second channel 132 toward the first channel 131, as shown in the drawing. With such communication channels 143 and 144 provided, the first liquid is permitted to easily flow from the first channel 131 toward the second channel 132, whereas the second liquid is permitted to easily flow from the second channel 132 toward the first channel 131, so that more uniform mixing between the first liquid and the second liquid can be achieved.

The gas channel 160 includes a gas delivery port 161 which is located at the distal end (tip) of the gas channel 160 and which functions as a gas mixing-in section, and a gas inflow port 163 which is located at the proximal end of the gas channel 160 and through which the gas flows into the gas channel 160. The gas delivery port 161 communicates with the flow lumen 150 through which the liquid mixture flows, and the gas supplied through the gas inflow port 163 flows through the gas delivery port 161 into the flow lumen 150.

The supply of the gas may be achieved, for example, by a method in which a gas supply source (not shown) as an external device is connected to the gas inflow port 163 through a known fluid-supplying tube, and the gas is supplied by use of the gas supply source. In the embodiment shown in the drawings, however, a method is adopted in which outside air is made to flow in by the venturi effect which will be described later. Adoption of such a method makes it possible to prevent the applicator 10 from becoming massive, as compared with the case of using a gas supply source. Incidentally, the gas to be used in the case of employing a gas supply source is not specifically restricted. Examples of the gas include air, nitrogen (inert gas), oxygen, and carbon dioxide (carbonic acid gas). In the medical elongated body 100, the gas delivery port 161 is so disposed that the gas is mixed into the liquid mixture formed by mixing of the first liquid and the second liquid. However, the gas is required only to be at least mixed into one of the first liquid, the second liquid and the liquid mixture at a position on the proximal side relative to the discharge port 180. As long as this requirement is met, the position where to dispose the gas delivery port 161 can be modified.

The flow lumen 150 located on the distal side (tip side) relative to the mixing section 140 may be provided with a constricted part 151 including a diametrically reduced part 153 where the diameter is gradually decreased along the distal direction and a diametrically enlarged part 155 which is continuous with the diametrically reduced part 153 and at which the diameter is gradually increased along the distal direction. The gas delivery port 161 of the gas channel 160 may communicate with the diametrically enlarged part 155, as shown in the drawing. When a liquid flows through the flow lumen 150, the pressure in the diametrically enlarged part 155 is reduced by the venturi effect, so that outside air can be driven to flow in through the gas inflow port 161. Besides, with the constricted part 151 provided, it is possible to prevent the gas mixed into the flow lumen 150 from flowing back toward the proximal side. Furthermore, the liquid mixture is accelerated when flowing from the diametrically reduced part 153 into the diametrically enlarged part 155, and part of the liquid is turned into spray form, whereby the quantity of bubbles contained in the liquid mixture can be increased. Consequently, foaming by the foaming member 170 can be promoted.

FIG. 5 shows an example of the foaming member 170 which can be used in this embodiment. As the foaming member 170, there can be used, for example, a member having a frame 171 and a mesh 173 mounted to the frame 171. The frame 171 is a member used to fix the mesh 173 to the flow lumen 150 of the medical elongated body 100. In addition, as shown in the drawing, the mesh 173 possessed by the foaming member 170 can be composed, for example, of a plurality of wire members 175 arranged in a grid pattern. The material forming the frame is not specifically restricted. Examples of the material usable include hard resin materials such as polyolefin resins such as polyethylene, polypropylene, etc., polyamides, polycarbonate, acrylic resins such as polymethyl methacrylate, etc., and metallic materials such as stainless steel, titanium, titanium alloys, etc. In addition, the material forming the wire members constituting the mesh is not particularly limited, and hard resin materials, metallic materials and the like can be used in the same manner as for the frame.

Furthermore, such factors as the interval of the grid pattern and the diameter of the wire members constituting the mesh are not specifically limited, and can be modified appropriately.

As shown in FIGS. 3 and 4, the discharge port 180 is composed of an opening provided at the distal end (tip) of the medical elongated body 100. The position(s) and the number of the foaming member(s) 170 to be arranged are not particularly limited; for example, the foaming member 170 may be disposed at least at the discharge port 180, as shown in the drawings. In addition, as shown, the discharge port 180 may be formed, for example, in the shape of being gradually increased in diameter along the distal direction, directly from the diametrically enlarged part 155 of the constricted part 151. In this case, it suffices that the material to be discharged can be discharged through the discharge port 180; therefore, the discharge port 180 is not specifically restricted in sectional shape or the like. For instance, the discharge port 180 may be composed of a straight-shaped opening which extends rectilinearly toward the distal side.

As shown in FIGS. 3 and 4, the medical elongated body 100 may be provided with an auxiliary mixing member 190 for further mixing of the liquid mixture formed by mixing of liquids in the mixing section 140. The auxiliary mixing member 190 may be disposed, for example, at the constricted part 151 of the flow lumen 150 possessed by the medical elongated body 100. In addition, as shown in FIG. 5, as the auxiliary mixing member 190, there can be used, for example, a member configured in the same manner as the foaming member 170, that is, a member having a frame 171 and a mesh 175. In this embodiment, since the auxiliary mixing member 190 is disposed at the constricted part 151, an auxiliary mixing member formed to be smaller than the foaming member 170 in outside diameter is used.

Now, operation of the medical elongated body 100 according to this embodiment will be described. The first liquid having flowed into the first channel 131 of the medical elongated body 100 and the second liquid having flowed into the second channel 132 are mixed with each other in the mixing section 140, to be the liquid mixture. The liquid mixture flows into the flow lumen 150 of the medical elongated body 100, and the gas is mixed into the liquid mixture in the gas mixing-in section 161. Then, when the liquid mixture with the gas mixed therein passes through the foaming member 170, bubbles (gas) contained in the liquid mixture are disintegrated minutely, whereby a foamed material to be discharged is produced which is composed of a multiplicity of foams. The foamed material to be discharged is discharged via the discharge port 180 of the medical elongated body 100.

Thus, when the first liquid and the second liquid differing in liquid composition are made to flow into the medical elongated body 100, a series of operations such as mixing of the liquids, mixing of the gas into the liquid, foaming of the liquid containing the gas mixed therein, and discharge of the foamed material to be discharged are carried out. Therefore, the use of the medical elongated body 100 makes it possible to omit the labor for operations necessary for production and discharge of the foamed material to be discharged. Consequently, it is ensured that various procedures for administering a foamed material to be discharged into a living body can be performed easily and speedily.

In addition, in the case where the mixing section 140 is provided with the plurality of communication channels 141 through which the first channel 131 and the second channel 132 communicate with each other, the first liquid and the second liquid can be mixed with each other through the plurality of communication channels 141 during the follow of the first liquid through the first channel 131 and during the flow of the second liquid through the second channel 132. Accordingly, the liquids can be mixed with each other in a favorable manner, without hampering smooth flow of the liquids inside the medical elongated body 100.

Besides, where the plurality of communication channels 141 include the first communication channels 143 gradually decreasing in channel sectional area from the first channel 131 toward the second channel 132 and the second communication channels 144 gradually decreasing in channel sectional area from the second channel 132 toward the first channel 131, the first liquid is permitted to easily flow from the first channel 131 toward the second channel 132, and the second liquid is permitted to easily flow from the second channel 132 toward the first channel 131. This ensures that the first liquid and the second liquid can be mixed uniformly with each other in the mixing section 140. Consequently, the concentrations of the ingredients of the material to be discharged can be prevented from scattering when the material is discharged as the foamed material to be discharged.

In addition, in the case where the foaming member 170 is at least disposed at the discharge port 180, the foaming of the liquid is brought about at the time of discharge. Therefore, it is possible to obviate a situation wherein the material to be discharged that is once foamed in the medical elongated body 100 might be liquefied, to be discharged as a liquid. Thus, assured discharge of a foamed material to be discharged can be achieved.

Furthermore, in the case where the medical elongated body 100 is provided further with the auxiliary mixing member 190 which is disposed on the distal side relative to the mixing section 140 and by which the liquid mixture is further mixed, the first liquid and the second liquid can be mixed with each other more uniformly.

Second Embodiment

Figure 6:
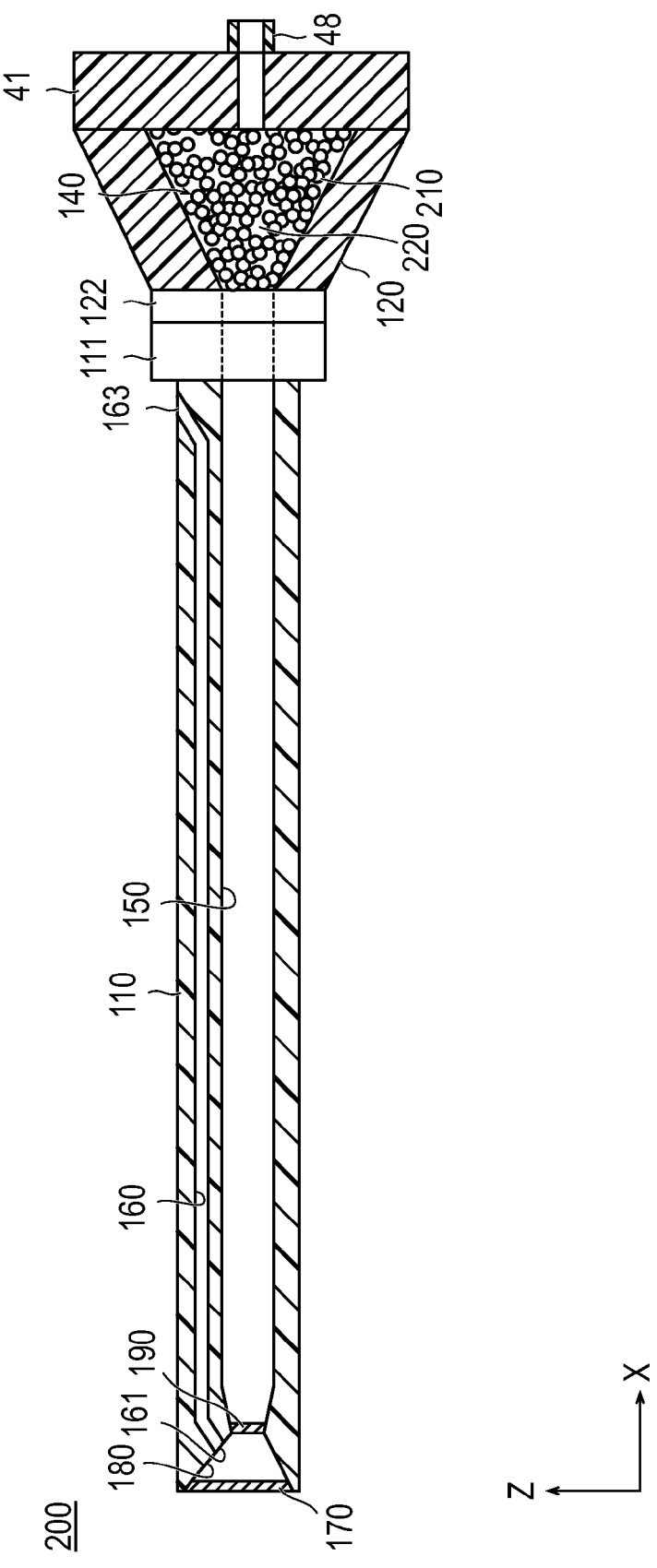
FIG. 6 is a partly sectional view for illustrating a medical elongated body according to a second embodiment of the present invention.
Figure 7:
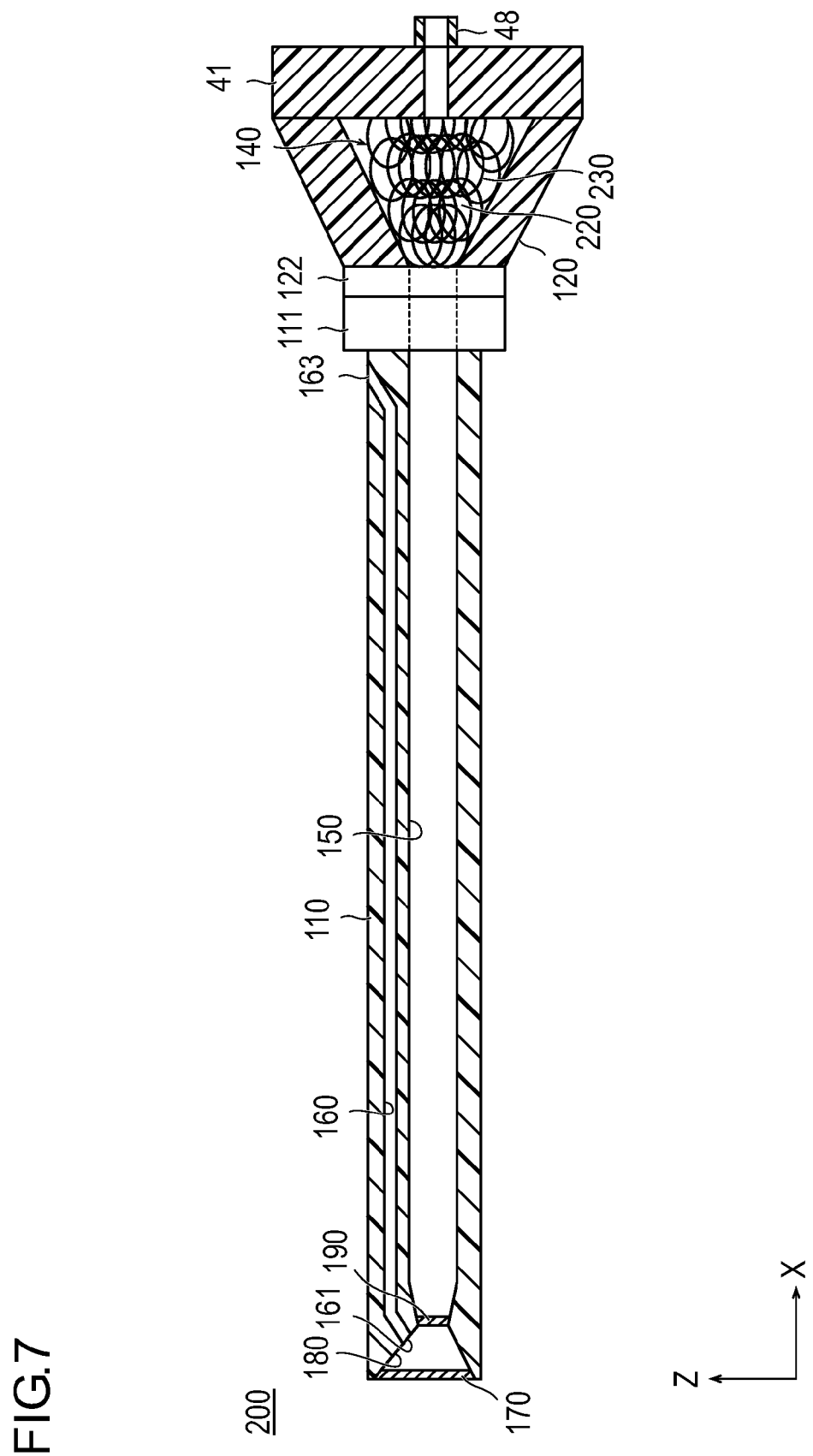
FIG. 7 is a partly sectional view for illustrating a medical elongated body according to a modification of the second embodiment.
Figure 8:
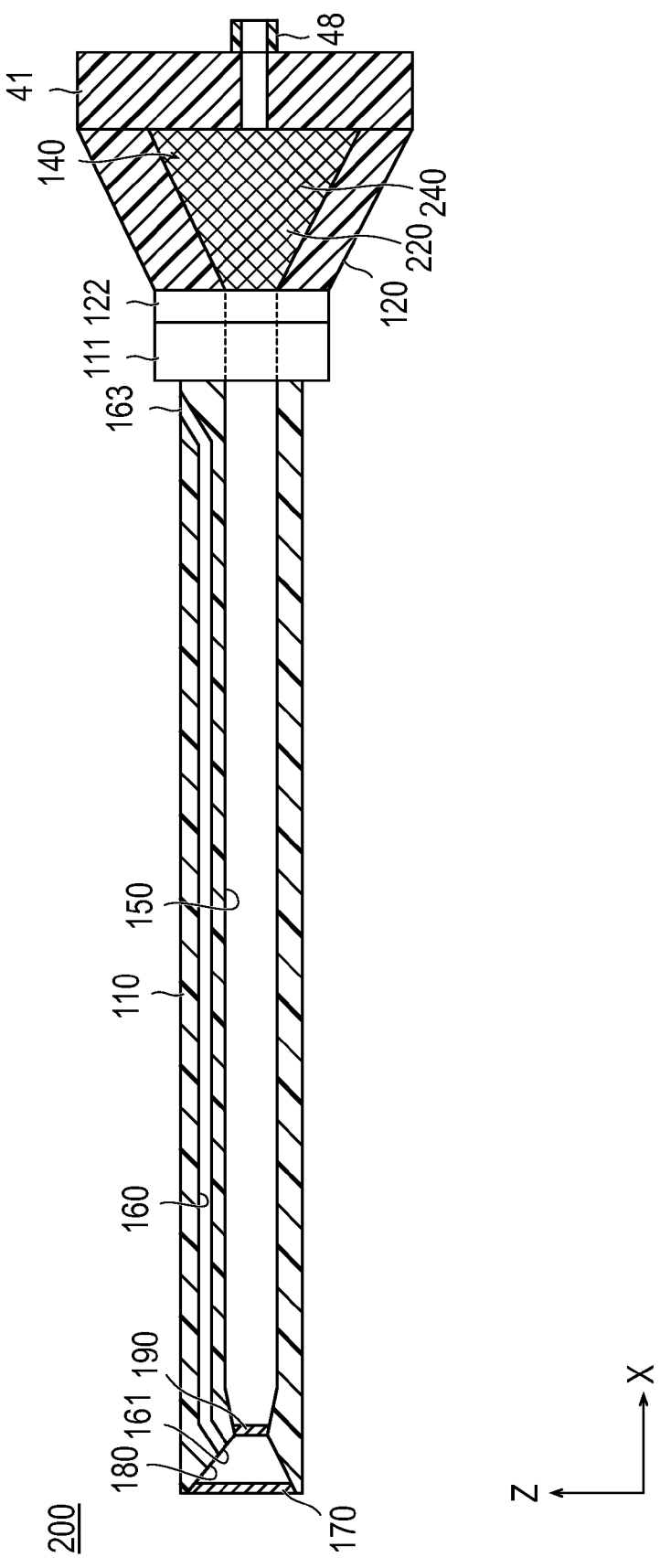
FIG. 8 is a partly sectional view for illustrating a medical elongated body according to another modification of the second embodiment.

Now, a medical elongated body 200 according to a second embodiment of the present invention will be described below, referring to FIGS. 6 to 8. In the drawings, the same members as those in the first embodiment are denoted by the same reference signs as used above, and descriptions of them will be omitted. FIG. 6 is a partly sectional view of the medical elongated body according to the second embodiment, FIG. 7 is a partly sectional view of a medical elongated body according to a modification of the second embodiment, and FIG. 8 is a partly sectional view of a medical elongated body according to another modification of the second embodiment.

In the medical elongated body 100 according to the first embodiment described above, the mixing section 140 in which the first liquid and the second liquid are mixed with each other is provided with the plurality of communication channels 141 for promoting the mixing of the first liquid and the second liquid. On the other hand, in the medical elongated body 200 according to this embodiment, a predetermined member for promoting mixing of a first liquid and a second liquid is disposed, in place of the communication channels 141. In this point, this embodiment differs from the above-described embodiment.

As shown in FIG. 6, granular members 210, for example, can be used as the member for promoting the mixing of the first liquid and the second liquid. Where a plurality of the granular members 210 are provided in a mixing section 140, a plurality of irregular channels 220 in which to mix the first liquid and the second liquid are formed between the granular members 210 in the mixing section 140. This ensures that the mixing of a liquid mixture in the process of flowing of the liquids through the mixing section 140 is promoted more, as compared with the case where the mixing is conducted by simply mixing one of the liquids into the flow of the other of the liquids. Consequently, it is possible to obtain a liquid mixture having been mixed more uniformly.

Incidentally, the material forming the granular members 210 is not specifically restricted. Examples of the material usable include resin materials such as polyolefin resins such as polyethylene, polypropylene, etc., polyamides, polycarbonate, acrylic resins such as polymethyl methacrylate, etc., polystyrene, fluoro-resins such as polytetrafluoroethylene, etc., and metallic materials such as stainless steel, titanium, titanium alloys, etc. In addition, the number and the diameter of the granular members 210 are not particularly limited, and can be modified so long as the granular members 210 can promote the mixing of the first liquid and the second liquid.

FIG. 7 illustrates a modification of the second embodiment. As shown in this modification, line-shaped members 230 shaped to be curved or wound like coils, for example, can be used as the member for promoting the mixing, in place of the granular members 210. In addition, FIG. 8 shows another modification of the second embodiment. As shown in this another modification, a brush-like member in which line-shaped members 240 in rectilinear form are extending in a plurality of different directions, for example, can also be used as the mixing-promoting member. Where such line-shaped members 230, 240 are used, also, the plurality of channels 220 in which to mix the first liquid and the second liquid can be formed in the mixing section 140. Consequently, the mixing of the liquid mixture can be promoted in the process of flowing of the liquids through the mixing section 140, like in the case where the granular members 210 are used.

Incidentally, the material forming each of the line-shaped members 230, 240 is not specifically restricted. Examples of the material which can be used include resin materials such as polyolefin resins such as polyethylene, polypropylene, etc., polyamides, polycarbonate, acrylic resins such as polymethyl methacrylate, etc., polystyrene, fluoro-resins such as polytetrafluoroethylene, etc., and metallic materials such as stainless steel, titanium, titanium alloys such as nickel-titanium alloy, etc., tantalum, tantalum alloys, tungsten, tungsten alloys, cobalt alloys, platinum alloys such as platinum-iridium, etc. Besides, the number and the diameter of the line-shaped members 230, 240 are not particularly limited, and can be modified insofar as the line-shaped members 230, 240 can promote the mixing of the first liquid and the second liquid.

Third Embodiment

Figure 9:
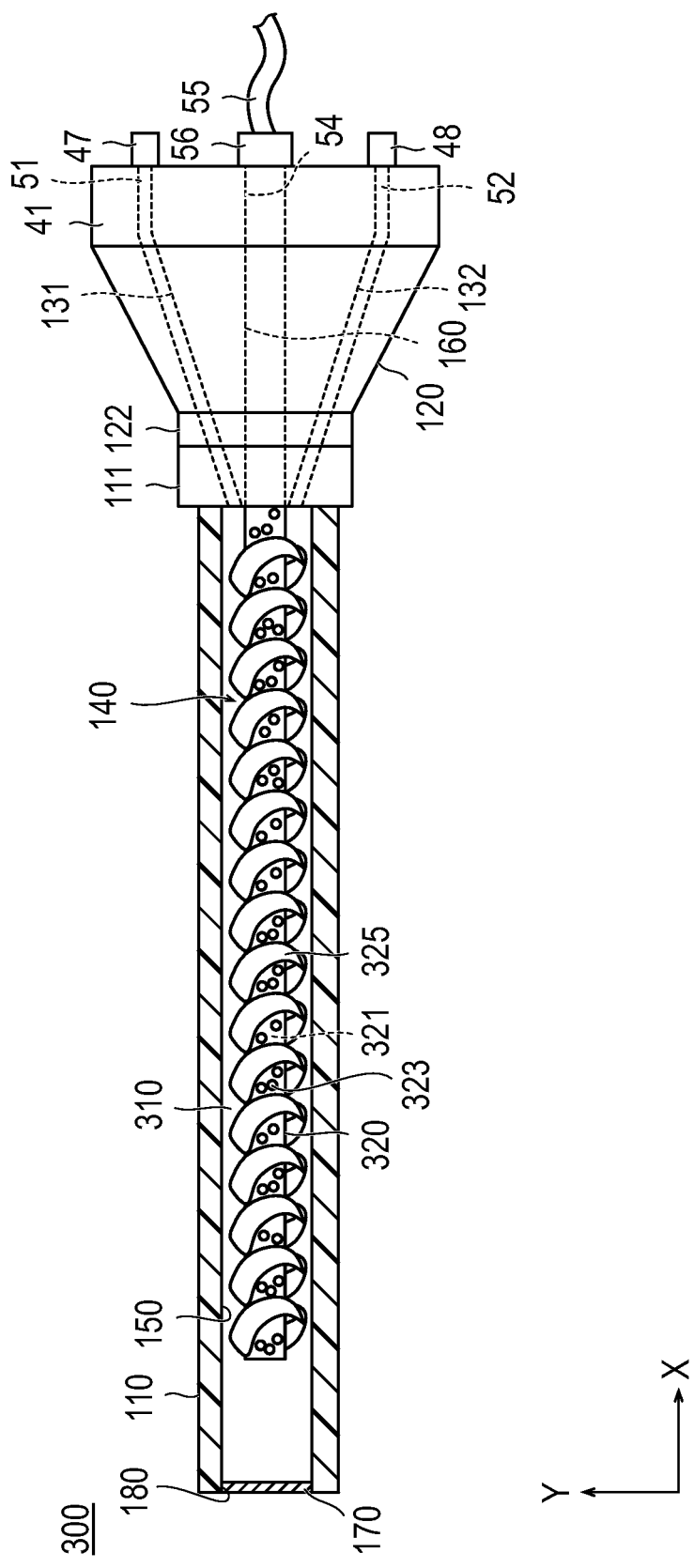
FIG. 9 is a partly sectional view for illustrating a medical elongated body according to a third embodiment of the present invention.

Now, referring to FIG. 9, a medical elongated body 300 according to a third embodiment of the present invention will be described below. In FIG. 9, the same members as those in each of the above-described embodiments are denoted by the same reference signs as used above, and descriptions of them will be omitted. FIG. 9 is a partly sectional view of the medical elongated body according to the third embodiment.

In the medical elongated body 300 according to this embodiment, a mixing section 140 in which to mix a first liquid and a second liquid is provided therein with a stirring channel 310 through which the first liquid and the second liquid and a gas are made to flow under stirring. With the stirring channel 310 thus provided in the medical elongated body 300, it is made possible to promote the mixing of the liquids in the mixing section 140, like in the case where the communication channels 141 are provided as shown in the first embodiment and in the case where the granular members 210 or the line-shaped members 230, 240 are provided as shown in the second embodiment.

As illustrated in FIG. 9, the medical elongated body 300 is provided in a connecting section 120 thereof with a first channel 131, a second channel 132, and a gas channel 160 through which to supply a gas to be mixed into the liquid. In addition, the mixing section 140 is provided in a body section 110 of the medical elongated body 300. Besides, a base portion 41 of an operating member 40 is provided therein with a channel 51 communicating with the first channel 131 in the medical elongated body 300, a channel 52 communicating with the second channel 132 in the medical elongated body 300, and a channel 54 communicating with the gas channel 160 in the medical elongated body 300. At the channel 54 provided in the base portion 41 of the operating member 40, there is provided a connecting member 56 to which a fluid-supplying tube 55 connected to a gas supply source (not shown) provided as an external device is connected in a liquid-tight and gas-tight manner. The supply of a gas into the gas channel 160 can be carried out through this tube 55.

In the body section 110 of the medical elongated body 300 is disposed a stirring member 320 for forming the stirring channel 310. The stirring member 320 includes a gas lumen 321 which is formed inside the stirring member 320 and communicates with the gas channel 160, a plurality of through-holes 323 piercing through the gas lumen 321 and an outer surface of the stirring member 320, and a stirring vane 325 arranged spirally around the outer surface of the stirring member 320. In addition, the stirring member 320 is so mounted as to be rotatable about an axis inside the body section 110 of the medical elongated body 300, and to form the stirring channel 310 between an inner wall of the body section 110 and the stirring member 320.

As the material forming the stirring member 320, there can be used, for example, the material forming the body section 110 of the medical elongated body 300. Besides, the number, layout and the like of the through-holes 323 provided in the stirring member 320 are not restricted to those shown in the drawing, and can be changed appropriately. The number, shape and the like of the stirring vane(s) 325 can also be changed as long as the stirring vane(s) 325 can effect mixing of the liquids and the gas.

Now, operation of the medical elongated body 300 according to this embodiment will be described. When a first liquid and a second liquid flow into the mixing section 140 of the medical elongated body 300, the stirring member 320 is rotated attendantly on the inflow of the liquids, whereby the first liquid and the second liquid are mixed with each other. In this instance, a gas is supplied into the mixing section 140 via the through-holes 323 of the stirring member 320. The first liquid, the second liquid and the gas flow toward a discharge port 180 while being stirred when passing through the stirring channel 310, and, accordingly, mixing of the liquids and the gas can be promoted.

Fourth Embodiment

Figure 10:
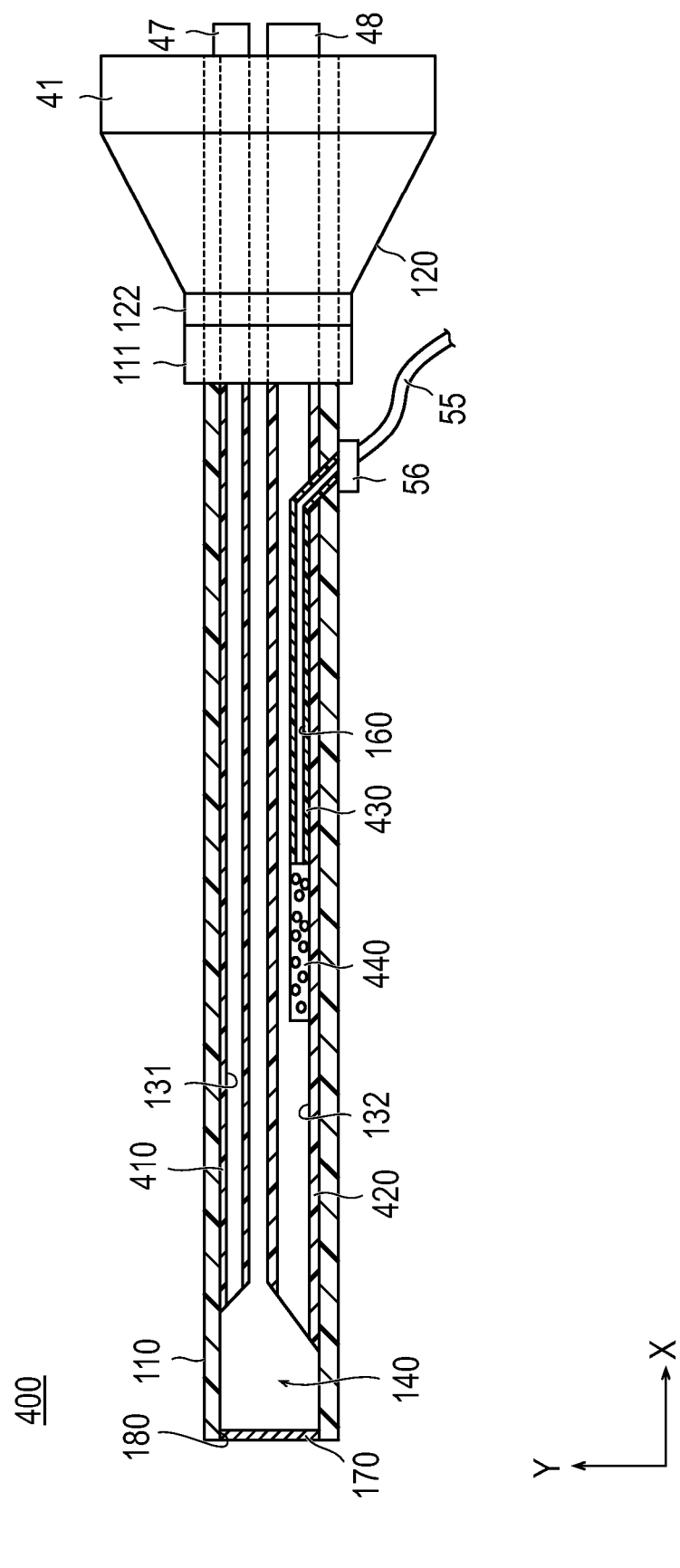
FIG. 10 is a partly sectional view for illustrating a medical elongated body according to a fourth embodiment of the present invention.

Now, referring to FIG. 10, a medical elongated body 400 according to a fourth embodiment of the present invention will be described below. In FIG. 10, the same members as those in the above-described embodiments are denoted by the same reference signs as used above, and descriptions of them will be omitted. FIG. 10 is a partly sectional view of the medical elongated body according to the fourth embodiment.

In the medical elongated body 400 according to this embodiment, a porous member 440 is disposed in a gas channel 160, and a gas released from the porous member 440 is mixed into liquids. This embodiment differs from the above-described embodiments in that such a porous member 440 is provided.

As shown in FIG. 10, the medical elongated body 400 is provided therein with: a first inner tube 410 provided therein with a first channel 131 through which a first liquid flows; a second inner tube 420 provided therein with a second channel 132 through which a second liquid flows; and a gas inner tube 430 provided therein with the gas channel 160 through which the gas flows. As shown in the drawing, for example, a distal opening of the first inner tube 410 is formed in the shape of an opening so inclined that the first liquid flows from the distal end of the first inner tube 410 toward the distal end side of the second inner tube 420. Similarly, a distal opening of the second inner tube 420 may be formed in the shape of an opening so inclined that the second liquid flows from the distal end of the second inner tube 420 toward the distal end side of the first inner tube 410.

To a distal portion of the gas inner tube 430, the porous member 440 is attached. In addition, that part of the gas inner tube 430 ranging from the distal portion to a predetermined portion is disposed inside the second channel 132 of the second inner tube 420, and the proximal end of the gas inner tube 430 is led out to the exterior via the second inner tube 420 and a body section 110 of the medical elongated body 400. At the proximal end of the gas inner tube 430, there is provided a connecting member 56 to which a fluid-supplying tube 55 connected to a gas supply source (not shown) provided as an external device is connected in a liquid-tight and gas-tight manner. The supply of a gas into the gas channel 160 can be carried out through this tube 55.

The porous member 440 mounted to the gas inner tube 430 is not specifically restricted. Examples of the porous member 440 include members obtained by a method wherein a hydrophobic resin material such as polytetrafluoroethylene, and olefin resins such as polypropylene, polyethylene, etc., a metallic material such as stainless steel, titanium, and titanium alloys represented by nickel-titanium, or a ceramic material or the like is subjected to a treatment for rendering the material porous.

As the material(s) forming the first inner tube 410, the second inner tube 400 and the gas inner tube 430, there can be used, for example, materials which are the same as or similar to those for forming the body section 110 of the medical elongated body 400.

Now, operation of the medical elongated body 400 according to this embodiment will be described. By the porous member 440 disposed inside the second channel 132 of the second inner tube 420, a gas in the form of a multiplicity of bubbles is dispersely mixed into the second liquid. Therefore, at the time of foaming a liquid mixture of the first liquid and the second liquid by a foaming member 170, the foaming can be promoted. Consequently, more assured discharge of a foamed material to be discharged can be achieved.

While the porous member 440 and the gas inner tube 430 are arranged in the second channel 132 of the second inner tube 420 in this embodiment, they may be disposed in the first channel 131 of the first inner tube 410, or may be arranged in both of the inner tubes 410 and 420. Furthermore, the porous member 440 and the gas inner tube 430 may be disposed in the mixing section 140.

Fifth Embodiment

Figure 11:
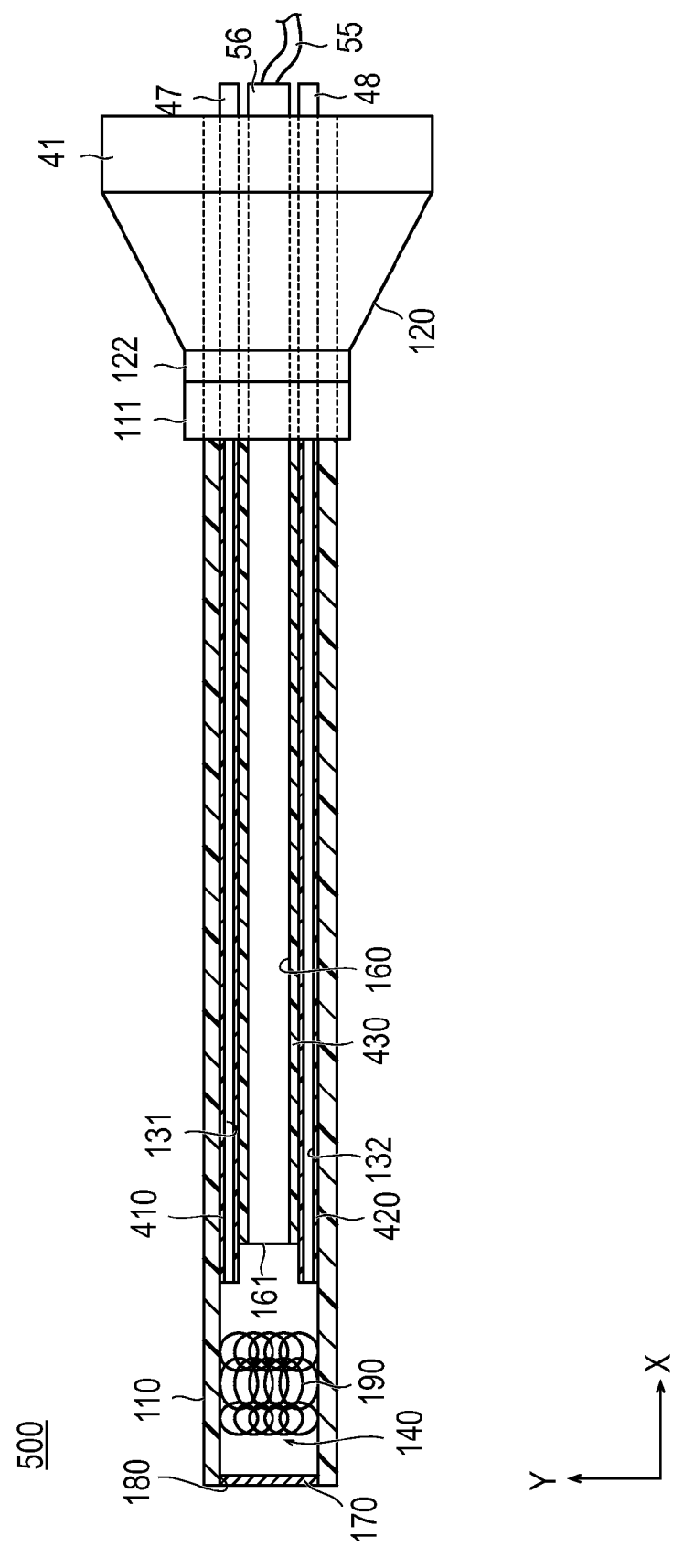
FIG. 11 is a partly sectional view for illustrating a medical elongated body according to a fifth embodiment of the present invention.

Now, referring to FIG. 11, a medical elongated body 500 according to a fifth embodiment of the present invention will be described below. In FIG. 11, the same members as those in the above-described embodiments are denoted by the same reference signs as used above, and descriptions of them will be omitted. FIG. 11 is a partly sectional view of the medical elongated body according to the fifth embodiment.

In the medical elongated body 500 according to this embodiment, a gas channel 160 is provided with a gas delivery port 161 through which a gas is delivered toward a mixing section 140, in which a first liquid and a second liquid are mixed, from the proximal side. This embodiment differs from the above-described embodiments in that such a gas delivery port 161 is provided.

As shown in FIG. 11, the gas delivery port 161 functioning as a gas mixing-in section is provided at the distal end of a gas inner tube 430. The gas delivery port 161 is arranged on the proximal side (in the axial direction of the medical elongated body 100) relative to the mixing section 140. Through the gas delivery port 161, the gas can be delivered at an arbitrary flow velocity by a gas supply source (not shown) provided as an external device and connected to the gas inner tube 430 through a fluid-supplying tube 55. The gas delivered via the gas delivery port 161 flows in the manner of distally passing through the mixing section 140. Incidentally, as shown in the drawing, an auxiliary mixing member 190 for more uniform mixing of a liquid mixture (mixture of the first liquid and the second liquid) may be provided in the mixing section 140 in which the first liquid and the second liquid are mixed with each other. Besides, as the auxiliary mixing member 190, for example, a line-shaped member or members composed of coils can be utilized.

Now, operation of the medical elongated body 500 according to this embodiment will be described. The gas is delivered through the gas delivery port 161 arranged on the proximal side relative to the mixing section 140, whereby the gas can be made to blow through the mixing section 140. Therefore, the liquid mixture can be prevented from stagnating or remaining in the mixing section 140. Consequently, the mixing section 140 can be prevented from being clogged up.

While the medical elongated body according to the present invention has been described above by way of the plurality of embodiments and modifications, the present invention is not to be restricted to the above-described embodiments and modifications but can be altered in various ways based on the descriptions in the claims. Further, the present invention can be carried out by combinations of the embodiments and modifications.

What is claimed is:

1. A medical elongated body by which a foamed material to be discharged is discharged, the medical elongated body comprising:
    a first channel through which a first liquid flows;
    a second channel through which a second liquid different from the first liquid in liquid composition flows;
    a mixing section at which the first channel and the second channel join and in which the first liquid and the second liquid are mixed;
    a gas channel through which a gas flows;
    a gas mixing-in section adapted to mix the gas into at least one of the first liquid flowing through the first channel and the second liquid flowing through the second channel or into a liquid mixture formed by mixing in the mixing section; and
    a discharge port through which a foamed material to be discharged is discharged;
    wherein the mixing section has a plurality of communication channels each establishing communication between the first channel and the second channel; and wherein the plurality of communication channels include a first communication channel of which channel sectional area gradually decreases from the first channel toward the second channel, and a second communication channel of which channel sectional area gradually decreases from the second channel toward the first channel.

2. The medical elongated body according to claim 1, further comprising an auxiliary mixing member which is disposed on a distal side relative to the mixing section and by which the liquid mixture is mixed.

3. The medical elongated body according to claim 1, further comprising a foaming member adapted to convert the liquid containing the gas mixed therein to the foamed material to be discharged.

4. The medical elongated body according to claim 3, wherein the foaming member is at least disposed at the discharge port.

5. The medical elongated body according to claim 3, wherein the gas mixing-in section comprises a gas delivery port adapted to deliver the gas from a position on a proximal side relative to the foaming member toward the foaming member.

* * * * *